US012623998B2

(12) United States Patent
Karafilidis et al.

(10) Patent No.: US 12,623,998 B2
(45) Date of Patent: May 12, 2026

(54) PROCESS FOR PREPARING A POLYISOCYANATE, POLYISOCYANATE, ITS USE AND POLYADDITION PRODUCTS PREPARED THEREFROM

(71) Applicant: Covestro Deutschland AG, Leverkusen (DE)

(72) Inventors: Christos Karafilidis, Leverkusen (DE); Marina Reithmeier, Cologne (DE); Stefan Wershofen, Mönchengladbach (DE); Michael Schedler, Leverkusen (DE); Michael Baecker, Korschenbroich (DE)

(73) Assignee: Covestro Deutschland AG, Leverkusen (DE)

( * ) Notice: Subject to any disclaimer, the term of this patent is extended or adjusted under 35 U.S.C. 154(b) by 478 days.

(21) Appl. No.: 18/256,219

(22) PCT Filed: Dec. 9, 2021

(86) PCT No.: PCT/EP2021/084975
    § 371 (c)(1),
    (2) Date: Jun. 7, 2023

(87) PCT Pub. No.: WO2022/122906
    PCT Pub. Date: Jun. 16, 2022

(65) Prior Publication Data
    US 2024/0018097 A1     Jan. 18, 2024

(30) Foreign Application Priority Data

Dec. 10, 2020    (EP) ..................................... 20213043
Sep. 3, 2021    (EP) ..................................... 21194917

(51) Int. Cl.
    *C07C 263/10*        (2006.01)
    *C07C 227/18*        (2006.01)
    *C07C 265/12*        (2006.01)
    *C08G 18/76*         (2006.01)
    *C08G 18/77*         (2006.01)

(52) U.S. Cl.
    CPC .......... *C07C 263/10* (2013.01); *C07C 227/18* (2013.01); *C07C 265/12* (2013.01); *C08G 18/7657* (2013.01); *C08G 18/771* (2013.01); *C07C 2527/10* (2013.01)

(58) Field of Classification Search
    CPC ... C07C 263/10; C07C 227/18; C07C 265/12; C08G 18/7657
    See application file for complete search history.

(56) References Cited

U.S. PATENT DOCUMENTS

| | | | |
|---|---|---|---|
| 3,808,250 A | 4/1974 | Kleimann et al. | |
| 3,929,863 A | 12/1975 | Blahak et al. | |
| 4,233,459 A | 11/1980 | Kilpper et al. | |
| 4,829,099 A | 5/1989 | Fuller et al. | |
| 5,998,538 A | 12/1999 | Meckel et al. | |
| 7,041,776 B2 * | 5/2006 | Koch ................... | C07C 209/78 564/333 |
| 7,923,574 B2 * | 4/2011 | Leimenstoll ....... | C08G 18/5039 564/45 |
| 7,985,479 B2 * | 7/2011 | Wamprecht .......... | C08G 18/482 428/423.1 |
| 10,173,969 B2 | 1/2019 | Jaeger et al. | |
| 10,731,187 B2 | 8/2020 | Jaeger et al. | |
| 11,155,844 B2 | 10/2021 | Jaeger et al. | |
| 2003/0212291 A1 | 11/2003 | Gajewski et al. | |
| 2010/0210748 A1 | 8/2010 | Leimenstoll et al. | |
| 2011/0004241 A1 | 1/2011 | Wintermantel et al. | |

OTHER PUBLICATIONS

Blahak, Von Johannes et al., "Estergruppen enthaltende Polyamine als Baukomponenten für die Polyurethanchemie" [Polyamines Containing Ester Groups as Structural Components for Polyurethane Chemistry], Angew. Makromol. Chem. 1972, 26, pp. 29-45.
Europäisches Arzneibuch [European Pharmacopoeia] 10.0., Deutscher Apotheker Verlag, 2020, ISBN 978-3-7692-7515-5, pp. 41-42.
International Search Report, PCT/EP2021/084975, date of mailing: Feb. 18, 2022, Authorized officer: Christian Wohnhaas.

* cited by examiner

*Primary Examiner* — Sikarl A Witherspoon
(74) *Attorney, Agent, or Firm* — Donald R. Palladino

(57)                    ABSTRACT

The present invention relates to a process for preparing a polyisocyanate, namely an isocyanate group-terminated polyol polyanthranilic acid ester. The process comprises the step of reacting an anthranilic acid derivative selected from anthranilic acid halide (in particular anthranilic acid chloride), isatoic anhydride or a mixture thereof with a first polyol of a number-average molar mass of at least 200 g/mol and a functionality in the range of 2 to 8, and obtaining, as a result, a polyamine (namely a polyol polyanthranilic acid ester with amine terminal groups) and reacting the polyamine with phosgene and obtaining, as a result, a polyisocyanate (namely an isocyanate group-terminated polyol polyanthranilic acid ester). The invention further relates to the polyisocyanates obtained in this way, their use in polyaddition reactions, and polyaddition products obtainable by these reactions.

15 Claims, No Drawings

PROCESS FOR PREPARING A POLYISOCYANATE, POLYISOCYANATE, ITS USE AND POLYADDITION PRODUCTS PREPARED THEREFROM

CROSS-REFERENCE TO RELATED APPLICATION

This application is a national stage application under 35 U.S.C. § 371 of PCT/EP2021/084975, filed Dec. 9, 2021, which claims the benefit of European Application No. 20213043.1, filed Dec. 10, 2020 and European Patent Application No. 21194917.7, filed Sep. 3, 2021, each of which is incorporated herein by reference.

FIELD

The present invention relates to a process for preparing a polyisocyanate, namely a polyol-polyanthranilic ester terminated by isocyanate groups. The process comprises the reaction of an anthranilic acid derivative selected from anthranoyl halide (especially anthranoyl chloride), isatoic anhydride or a mixture thereof with a first polyol of a number-average molar mass of at least 200 g/mol and functionality in the range from 2 to 8 to obtain a polyamine (namely a polyol-polyanthranilic ester having aminic end groups) and reacting the polyamine with phosgene to obtain a polyisocyanate (namely a polyol-polyanthranilic ester terminated by isocyanate groups). The invention further relates to the polyisocyanates thus obtainable, to the use thereof in polyaddition reactions, and to polyaddition products thus obtainable.

BACKGROUND

Polyurethane prepolymers containing isocyanate groups (=polyurethane structures having reactive NCO end groups) have long been known in the prior art. They are obtained by reacting a stoichiometric excess of a polyisocyanate component (for example methylene diphenylene diisocyanate, optionally in a mixture with higher homologs thereof, the polyphenylene polymethylene polyisocyanates) with a polyol component (for example a polyester polyol, a polyesterether polyol or a mixture of different polyol types), and are used, for example, in the production of elastomers, coatings, bonding agents and the like. In general, the aim is to keep the residual content of unconverted polyisocyanate component as low as possible in order not to impair later use and to prevent volatilization of volatile polyisocyanates during use. There has been no lack of attempts to improve the preparation of polyurethane prepolymers in such a way that such problems do not occur or are at least minimized. For this purpose, it is common practice, for example, to free the crude products from the prepolymer synthesis of residual constituents of polyisocyanate component used by thin-film distillation, which is energy-intensive and costly. For example, EP-A 0 590 398 describes the use of low-monomer isocyanate-terminated polyurethane prepolymers that have been obtained by removing the monomeric polyisocyanates by distillation. However, the fundamental procedure for preparation of prepolymers with NCO end groups has been retained. By contrast, the present invention takes an alternative route that likewise leads to NCO-terminated prepolymers, but does so not by the customary route of urethanization of low molecular weight polyisocyanates with a deficiency of polyols, but rather proceeding from reactive derivatives of anthranilic acid.

It is known that anthranilic acid can be converted to polyanthranilic esters, and such polyanthranilic esters can be used in polyaddition reactions, for instance as crosslinkers, as chain extenders or as reactant in the preparation of polyureas. For instance, the following publications describe the following:

the article "*Estergruppen enthaltende Polyamine als Baukomponenten für die Polyurethanchemie*"[Polyamines Containing Ester Groups as Structural Components for Polyurethane Chemistry] in Angew. Makromol. Chem. 1972, 26, 29-45: the use of such esters as structural components for polyurethane elastomers, US patent application US 2003/0212291 A1: the use thereof as crosslinkers, German patent specification DE 20 40 644: the use thereof as chain extenders, and US patent specification U.S. Pat. No. 3,808,250: the use thereof as amine component in the preparation of polyureas by reaction with isocyanates.

WO 89/00589 A1 (also published as U.S. Pat. No. 4,829, 099 and DE 38 51 428 T2) relates to adhesives produced from metabolically compatible polyisocyanate or polyisothiocyanate monomers. More particularly, this document relates to surgical adhesive polymers derived from these polyisocyanate monomers, which are not metabolized to give toxic products. One example of a possible route to such products which is described is the reaction of a polyhydric alcohol with an aromatic nitro acid chloride (for instance 2—and especially 4-nitrobenzoyl chloride), followed by catalytic hydrogenation of the nitro group to an amine group and phosgenation thereof to give an isocyanate group. (It is not possible to perform the catalytic hydrogenation before the reaction with the polyhydric alcohol because the acid chloride group in that case would be reduced to an aldehyde or even an alcohol group.) This synthesis route is complex and associated with not inconsiderable yield losses. The amines obtained as intermediates after the hydrogenation are comparatively high-melting solids (e.g. bis(2-aminobenzoyl)tetraethylene glycol with a melting range from 98° C. to 102° C.), which is disadvantageous for industrial applications on account of their difficulty of handling. The isocyanates obtained therefrom are generally high-viscosity oils, which is again disadvantageous for processability in industrial applications.

The problem mentioned at the outset of providing NCO-terminated prepolymers, if at all possible without fractions of the polyisocyanate component used, is not solved by the prior art cited. It would additionally be desirable for a preparation process for NCO-terminated prepolymers to be of minimum complexity and for the desired products (and the primary amines obtained as intermediates) to be provided in maximum yields and in an industrially readily processible form (liquid with not too high a viscosity).

There was therefore a need for further improvements in this field.

SUMMARY

Taking account of the need outlined, therefore, the present invention firstly provides a process for preparing a polyisocyanate, namely a polyol-polyanthranilic ester terminated by isocyanate groups. The process comprises the steps of:

(A) reacting an anthranilic acid derivative (which may be prepared from anthranilic acid obtained by fermentation) selected from anthranoyl halide (especially anthranoyl chloride), isatoic anhydride or a mixture thereof with a first polyol of functionality b and the general formula X—(OH)$_b$, where b is in the range from 2 to 8 and X is a radical that derives from the first polyol by removal of all alcohol groups, and where the first polyol has a number-average molar mass of at least 200 g/mol (calculated from the hydroxyl number determined to DIN 53240-2 (2007-11) and functionality b), to obtain a polyamine (namely a polyol-polyanthranilic ester having aminic end groups) of the formula $$H_2N-(ortho\text{-}C_6H_4)-(CO)-O-X-[-O-(CO)-(ortho\text{-}C_6H_4)-NH_2]_a$$

in which $a=b-1$; and (B) reacting the polyamine with phosgene to obtain a polyisocyanate (namely a polyol-polyanthranilic ester terminated by isocyanate groups) of the formula $$OCN-(ortho\text{-}C_6H_4)-(CO)-O-X-[-O-(CO)-(ortho\text{-}C_6H_4)-NCO]_a.$$

The present invention secondly provides a polyisocyanate (namely a polyol-polyanthranilic ester terminated by isocyanate groups) of the formula $$OCN-(ortho\text{-}C_6H_4)-(CO)-O-X-[-O-(CO)-(ortho\text{-}C_6H_4)-NCO]_a$$

in which

X is a radical which derives from a first polyol having functionality b and the general formula X—$(OH)_b$, where b is in the range from 2 to 8, by removal of all alcohol groups, in which a=b-1, and where the first polyol has a number-average molar mass (calculated from the hydroxyl number determined to DIN 53240-2 (2007-11) and functionality b) of at least 200 g/mol. The polyisocyanate is especially obtainable by the process of the invention and therefore, in the case of employment of the abovementioned possible embodiment with use of an anthranilic acid derivative produced from fermentatively obtained anthranilic acid, has a considerable proportion by mass, of up to 46% in particular, of biogenic carbon.

The present invention thirdly provides for the use of the polyisocyanate of the invention for production of a polyaddition product by reaction with a compound comprising 2 or more acidic hydrogen atoms.

Finally, the present invention fourthly provides the polyaddition products formed from the polyisocyanate of the invention and a compound comprising 2 or more acidic hydrogen atoms.

DESCRIPTION

Entirely surprisingly, it has been found that the phosgenation of polyol-polyanthranilic esters that derive from not excessively short-chain polyols (number-average molar mass at least 200 g/mol) leads to NCO-terminated products that are suitable for applications for which NCO-terminated polyurethane prepolymers have typically been used to date, where the problem of minimizing the residual content of unconverted polyisocyanate component cannot occur at all, because no such polyisocyanate component is even used. This is because the polymeric properties of the polyol-polyanthranilic esters terminated by isocyanate groups that have been produced by the process of the invention do not originate from a polyurethane structure, but are based on the polymeric structure of the first polyol X—$(OH)_b$ used. Therefore, the polyol-polyanthranilic esters terminated by isocyanate groups that have been produced in accordance with the invention can also be referred to as polyol prepolymers terminated by isocyanate groups.

In the terminology of the present invention, "b" denotes the functionality of the first polyol. This is understood to mean the functionality of the starter used in the preparation of the polyol, without taking account of any reduction in that functionality as a result of side reactions in the preparation of the first polyol.

Number-average molar mass ($M_n$, reported in g/mol) is calculated in the context of the present invention from hydroxyl number (OH N, reported in mg/g["mg KOH per g of sample analyzed"]) and functionality b according to $$M_n/(g\cdot mol^{-1}) = [56106\cdot b]/[OHN/(mg\cdot g^{-1})].$$

The crucial method for the determination of hydroxyl number here is DIN 53240-2 (2007-11).

There now follows a brief summary of various possible embodiments of the invention.

In a first embodiment of the process of the invention, which can be combined with all other embodiments, b is in the range from 2 to 4.

In a second embodiment of the process of the invention, which can be combined with all other embodiments, the first polyol has a number-average molar mass in the range from 200 g/mol to 25,000 g/mol, preferably in the range from 200 g/mol to 4000 g/mol, more preferably in the range from 200 g/mol to 1200 g/mol.

In a third embodiment of the process of the invention, which can be combined with all other embodiments, the first polyol is selected from a polyether polyol, a polyester polyol, a polyetherester polyol, a polycarbonate polyol, a polyether polycarbonate polyol, a polythioether polyol or a mixture of two or more of the aforementioned polyols.

In a fourth embodiment of the process of the invention, which can be combined with all other embodiments, the first polyol is selected from a polyether polyol, a polyetherester polyol, a polyether polycarbonate polyol or a mixture of two or more of the aforementioned polyols.

In a fifth embodiment of the process of the invention, which is a particular configuration of the fourth embodiment, the content of unsaturated end groups in the first polyol is in the range from 0 meq/g to 0.040 meq/g, preferably in the range from 0 meq/g to 0.035 meq/g and more preferably in the range from 0 meq/g to 0.030 meq/g.

In a sixth embodiment of the process of the invention, which is a particular configuration of the fourth and fifth embodiments, the first polyol has polyether groups based on ethylene oxide and/or propylene oxide.

In a seventh embodiment of the process of the invention, which is a particular configuration of the fourth to sixth embodiments, the first polyol has polyether groups that have been obtained by polyaddition of a cyclic ether onto a starter compound selected from water, a polyamine, a second polyol having a number-average molar mass of less than 200 g/mol, or a mixture of two or more of the aforementioned starter compounds.

In an eighth embodiment of the process of the invention, which is a particular configuration of the seventh embodiment, the polyaddition is mediated by a double metal cyanide catalyst.

In a ninth embodiment of the process of the invention, which is a further particular configuration of the seventh embodiment, the polyaddition is mediated by a base catalyst.

In a tenth embodiment of the process of the invention, which is a further particular configuration of the seventh embodiment, the polyaddition is mediated by a double metal cyanide catalyst and by a base catalyst.

In an eleventh embodiment of the process of the invention, which can be combined with all other embodiments, the reaction of the anthranilic acid derivative with the first polyol is conducted in the presence of a basic catalyst.

In a twelfth embodiment of the process of the invention, which is a particular configuration of the eleventh embodiment, the basic catalyst is selected from an alkali metal hydroxide, an alkaline earth metal hydroxide, an alkali metal carbonate, an alkaline earth metal carbonate, an alkali metal hydrogencarbonate, an alkaline earth metal hydrogencarbonate, a phosphate, a phosphonate, an amine, a diamine, a polyamine or a mixture of two or more of the aforementioned catalysts.

In a thirteenth embodiment of the process of the invention, which can be combined with all other embodiments, the reacting of the anthranilic acid derivative with the first polyol is conducted at a temperature in the range from 0° C. to 120° C., preferably from 20° C. to 115° C. and more preferably from 35° C. to 110° C.

In a fourteenth embodiment of the process of the invention, which can be combined with all other embodiments, a gas ($CO_2$ or hydrogen halide, especially HCl) formed in step (A) is removed in gaseous form, chemically bound or physically bound during the reaction of the anthranilic acid derivative with the first polyol.

In a fifteenth embodiment of the process of the invention, which can be combined with all other embodiments, the reaction of the anthranilic acid derivative with the first polyol is conducted in the presence of a solvent, where the solvent is selected from acetone, tetrahydrofuran, diethyl ether, dimethylformamide, dimethylacetamide, an aliphatic hydrocarbon (such as, in particular, hexane, heptane, octane or a mixture of two or more of the aforementioned aliphatic hydrocarbons), an aromatic hydrocarbon (such as, in particular, benzene, toluene or a mixture of the two), a chlorinated aliphatic solvent (especially dichloromethane, chloroform, carbon tetrachloride or a mixture of two or more of the aforementioned chlorinated aliphatic solvents) or a chlorinated aromatic solvent (such as, in particular, chlorobenzene, dichlorobenzene or a mixture of the two).

In a sixteenth embodiment of the process of the invention, which is a particular configuration of the fifteenth embodiment, the polyamine is obtained as a solution in the solvent (solution polymerization).

In a seventeenth embodiment of the process of the invention, which is a further particular configuration of the fifteenth embodiment, the polyamine is obtained as a suspension in the solvent (suspension polymerization).

In an eighteenth embodiment of the process of the invention, which can be combined with all other embodiments, provided that these do not necessarily require the use of a solvent in step (A), the reaction of the anthranilic acid derivative with the first polyol is conducted in the absence of a solvent (bulk or mass polymerization).

In a nineteenth embodiment of the process of the invention, which can be combined with all other embodiments, the polyamine obtained in step (A) is isolated by a method selected from filtration, distillation, sublimation, crystallization, precipitation or a combination of two or more of the aforementioned methods.

In a twentieth embodiment of the process of the invention, which can be combined with all other embodiments, the reaction of the polyamine with phosgene in step (B) is conducted at a temperature in the range from 0° C. to 200° C., preferably 5° C. to 180° C., more preferably 5° C. to 150° C.

In a twenty-first embodiment of the process of the invention, which can be combined with all other embodiments, phosgene is used in step (B) in a stoichiometric excess based on the amino groups of the polyamine.

In a twenty-second embodiment of the process of the invention, which can be combined with all other embodiments, the reaction of the polyamine with phosgene in step (B) is performed in the presence of a solvent, where the solvent is selected from toluene, xylene, chlorobenzene, dichlorobenzene (especially the ortho isomer), dioxane, methylene chloride, perchloroethylene, trichlorofluoromethane or a mixture of two or more of the aforementioned solvents.

In a twenty-third embodiment of the process of the invention, which can be combined with all other embodiments, the isatoic anhydride is obtained by reacting anthranilic acid with carbon monoxide in the presence of a catalyst (especially in the presence of a Pd or Pt catalyst), a phosgenation medium selected from phosgene, diphosgene, triphosgene, oxalyl chloride or a mixture of two or more of the aforementioned phosgenation media or with 1,1-carbonyldiimidazole and/or dimethyl carbonate.

In a twenty-fourth embodiment of the process of the invention, which can be combined with all other embodiments, the anthranoyl halide is anthranoyl chloride, which is obtained by reacting anthranilic acid with a chlorinating reagent (such as, in particular, thionyl chloride).

In a twenty-fifth embodiment of the process of the invention, which is a particular configuration of the twenty-third and twenty-fourth embodiments, the anthranilic acid is obtained by fermenting a raw material comprising a fermentable carbon compound and a nitrogen compound.

In a twenty-sixth embodiment of the process of the invention, which is a particular configuration of the twenty-fifth embodiment, the fermentable carbon compound comprises starch hydrolyzate, sugarcane juice, sugarbeet juice and/or hydrolyzates of lignocellulosic raw materials, wherein the nitrogen compound comprises gaseous ammonia, aqueous ammonia, ammonium salts and/or urea.

In a twenty-seventh embodiment of the process of the invention, which can be combined with all other embodiments, provided that they do not include step (C)(ii) described further down, step (B) is followed by:

(C)(i) reacting the polyisocyanate obtained in step (B) with an organic compound comprising 2 or more acidic hydrogen atoms to obtain a polyaddition product.

In a twenty-eighth embodiment of the process of the invention, which is a particular configuration of the twenty-seventh embodiment, the organic compound comprising 2 or more acidic hydrogen atoms comprises a third polyol (and, in particular, is a third polyol), wherein the polyaddition product obtained is a polyurethane elastomer, a polyurethane thermoplastic, a polyurethane foam, a polyurethane adhesive or a polyurethane sealant.

In a twenty-ninth embodiment of the process of the invention, which is a particular configuration of the twenty-seventh embodiment, the organic compound comprising 2 or more acidic hydrogen atoms comprises a polyamine (and, in particular, is a polyamine), wherein the polyaddition product obtained is a polyurea elastomer, a polyurea thermoplastic, a polyurea foam, a polyurea adhesive or a polyurea sealant.

It is likewise possible to combine the twenty-eighth and twenty-ninth embodiments with one another in such a way that the organic compound comprising 2 or more acidic hydrogen atoms comprises a third polyol and a polyamine, in which case the polyaddition product obtained is an elastomer, a thermoplastic, a foam, an adhesive or a sealant having mixed urethane and urea structures.

In a thirtieth embodiment of the process of the invention, which can be combined with all other embodiments, provided that they do not include step (C)(i), step (B) is followed by:

(C)(ii) reacting the polyisocyanate obtained in step (B) with (a substoichiometric amount of) water (in relation to the isocyanate groups present) to obtain a foam, adhesive or sealant.

In a thirty-first embodiment of the process of the invention, which is a particular configuration of the thirtieth embodiment, the water comes from a gas atmosphere that surrounds the polyisocyanate, or from a substrate on which the polyisocyanate is present.

In a first embodiment of the polyisocyanate of the invention, which can be combined with all other embodiments, b is in the range from 2 to 4.

In a second embodiment of the polyisocyanate of the invention, which can be combined with all other embodiments, the first polyol has a number-average molar mass in the range from 200 g/mol to 25,000 g/mol, preferably in the range from 200 g/mol to 4000 g/mol, more preferably in the range from 200 g/mol to 1200 g/mol.

In a third embodiment of the polyisocyanate of the invention, which can be combined with all other embodiments, the first polyol is selected from a polyether polyol, a polyester polyol, a polyetherester polyol, a polycarbonate polyol, a polyether polycarbonate polyol, a polythioether polyol or a mixture of two or more of the aforementioned polyols.

In a fourth embodiment of the polyisocyanate of the invention, which can be combined with all other embodiments, the first polyol is selected from a polyether polyol, a polyetherester polyol, a polyether polycarbonate polyol or a mixture of two or more of the aforementioned polyols.

In a fifth embodiment of the polyisocyanate of the invention, which is a particular configuration of the fourth embodiment, the content of unsaturated end groups in the first polyol is in the range from 0 meq/g to 0.02 meq/g, preferably in the range from 0 meq/g to 0.015 meq/g, more preferably in the range from 0 meq/g to 0.01 meq/g.

In a sixth embodiment of the polyisocyanate of the invention, which is a particular configuration of the fourth and fifth embodiments, the first polyol has polyether groups based on ethylene oxide and/or propylene oxide.

In a seventh embodiment of the polyisocyanate of the invention, which is a particular configuration of the fourth to sixth embodiments, the first polyol has polyether groups that are obtainable by polyaddition onto starter compounds selected from water, a polyamine, a second polyol having a number-average molar mass of less than 200 g/mol, or a mixture of two or more of the aforementioned starter compounds.

In an eighth embodiment of the polyisocyanate of the invention, which can be combined with all other embodiments, the polyisocyanate has a proportion by mass of biogenic carbon based on its total mass in the range from 0.60% to 46%, preferably from 1.5% to 43%, more preferably from 7.0% to 41%. The crucial test method here is ASTM D 6866-21 (DOI:

In one embodiment of the use of the invention, the compound comprising 2 or more acidic hydrogen atoms comprises a third polyol, a polyamine and/or water.

In one embodiment of the polyaddition product of the invention, the compound comprising 2 or more acidic hydrogen atoms comprises a third polyol, a polyamine and/or water.

The embodiments briefly outlined above and further possible embodiments of the invention are elucidated in detail hereinafter. All embodiments and other configurations may be combined with one another as desired unless stated otherwise or unambiguously apparent from the context.

In relation to the process of the invention, reference is made to the following details:

Reaction of the Anthranilic Acid Derivative with the First Polyol (Step (a))

The first polyol to be used in step (A) of the process of the invention has a functionality in the range from 2 to 8, preferably 2 to 4, and has a number-average molar mass of at least 200 g/mol, preferably in the range from 200 g/mol to 25,000 g/mol, more preferably in the range from 200 g/mol to 4000 g/mol, and most preferably in the range from 200 g/mol to 1200 g/mol. The first polyol may also be a mixture of two or more polyols; in that case, the aforementioned values of functionality and number-average molar mass relate to the corresponding averages of the mixture. But even in the case of a polyol mixture as "first polyol", each individual polyol present in the mixture must have the properties that are essential in accordance with the invention of a number-average molar mass of at least 200 g/mol and a functionality b in the range from 2 to 8.

Particularly suitable polyols are the following that are known per se in the specialist field: polyether polyols, polyester polyols, polyetherester polyols, polycarbonate polyols, polyether polycarbonate polyols, polythioether polyol, and mixtures thereof.

Polyols having polyether groups (i.e. polyether polyols, polyetherester polyols, polyether polycarbonate polyols and mixtures thereof) are particularly preferred. Such polyether groups are preferably obtained by polyaddition, as known per se, of cyclic ethers onto a starter compound such as water, a polyamine, a second polyol having a number-average molar mass of less than 200 g/mol, or a mixture of two or more of these. Cyclic ethers here are preferably ethylene oxide and/or propylene oxide.

Such a polyaddition for preparation of polyols having polyether groups may, as is known in the specialist field, be catalyzed by a double metal cyanide (DMC) catalyst, by a base catalyst, or by a combination of the two (especially further base-catalyzed alkoxylation of a polyol obtained by DMC catalysis).

The first polyol to be used in the process of the invention preferably has a content of unsaturated end groups in the range from 0 meq/g to 0.040 meq/g, more preferably in the range from 0 meq/g to 0.035 meq/g and most preferably in the range from 0 meq/g to meq/g. The method of determination which is crucial in this context is ASTM D2849-69 (1969-12-19).

The anthranilic acid derivative to be used in step (A) of the process of the invention may be isatoic anhydride and/or an anthranoyl halide, especially anthranoyl chloride.

Anthranoyl halides can be obtained by reacting anthranilic acid with a suitable halogenating reagent, as is known in the specialist field and therefore does not need to be set out in detail at this point. Among the anthranoyl halides, preference is given to anthranoyl chloride. This is especially obtained by reaction of anthranilic acid with thionyl chloride.

However, isatoic anhydride is preferred and is especially obtained by reacting anthranilic acid with carbon monoxide in the presence of a catalyst (especially in the presence of a Pd or Pt catalyst),
a phosgenation medium selected from phosgene, diphosgene, triphosgene, oxalyl chloride or a mixture of two or more of the aforementioned phosgenation media
or with 1,1-carbonyldiimidazole and/or dimethyl carbonate.

The starting point for the obtaining both of the anthranoyl halides and of isatoic anhydride is thus preferably anthranilic acid. The production of anthranilic acid is known in the technical field and can be effected "chemically" or by fermentation (biotechnology):

The chemical preparation of anthranilic acid is described in the literature. An example of a suitable synthesis route is the reaction of phthalimide with sodium hypochlorite. Phthalimide can itself be obtained from phthalic anhydride and ammonia. A suitable process for preparing anthranilic acid is described, for example, in EP 0 004 635 A2.

The fermentative production of anthranilic acid, which is preferred in the context of the present invention, makes use of the fact that, in the metabolism of bacteria and yeasts, anthranilic acid is formed in the shikimic acid pathway as a natural intermediate in the synthesis of tryptophan. In the biotechnological production of anthranilic acid, the conversion thereof in the metabolic pathway is reduced or suppressed in order to achieve accumulation in the fermentation medium. Such a concept for biotechnological production of anthranilic acid is described in international patent applications WO 2015/124686 A1 and WO 2015/124687 A1. A possible recombinant microorganism described is the use of bacteria from the families of the corynebacteria or pseudomonads. A more recent application (WO 2017/102853 A1) describes the use of yeasts.

Preferably, the anthranilic acid is therefore obtained by fermenting a raw material containing a fermentable carbon compound and a nitrogen compound in the presence of microorganisms. The fermentable carbon compound preferably comprises starch hydrolyzate, sugarcane juice, sugarbeet juice and/or hydrolyzates of lignocellulosic raw materials, and the nitrogen compound preferably comprises gaseous ammonia, aqueous ammonia, ammonium salts and/or urea. The microorganisms preferably comprise those described in the above-cited literature references, i.e. *Escherichia coli, Pseudomonas putida, Corynebacterium glutamicum, Ashbya gossypii, Pichia pastoris, Hansenula polymorpha, Yarrowia lipolytica, Zygosaccharomyces bailiff* or *Saccharomyces cerevisiae.*

The reaction of the anthranilic acid derivative with the first polyol is preferably effected in the presence of a catalyst, especially when the anthranilic acid derivative used is isatoic anhydride. Suitable basic catalysts are especially alkali metal hydroxides, alkaline earth metal hydroxides, alkali metal carbonates, alkaline earth metal carbonates, alkali metal hydrogencarbonates, alkaline earth metal hydrogencarbonates, phosphates, phosphonates, (mono)amines, diamines, polyamines or mixtures of two or more of the aforementioned catalysts.

The temperature for the reaction of the anthranilic acid derivative with the first polyol is preferably in the range from 0° C. to 120° C., more preferably from 20° C. to 115° C. and most preferably from 35° C. to 110° C.

The reaction in step (A) results in evolution of gas ($CO_2$ in the case of isatoic anhydride, and hydrogen halide in the case of anthranoyl halides). This gas may be removed in gaseous form, chemically bound or physically bound.

The reaction of the anthranilic acid derivative with the first polyol can be conducted in the presence or absence (bulk or mass polymerization) of a solvent. If the reaction is effected in the presence of a solvent, it is preferably selected from acetone, tetrahydrofuran, diethyl ether, dimethylformamide, dimethylacetamide, an aliphatic hydrocarbon (such as, in particular, hexane, heptane, octane or a mixture of two or more of the aforementioned aliphatic hydrocarbons), an aromatic hydrocarbon (such as, in particular, benzene, toluene or a mixture of the two), a chlorinated aliphatic solvent (especially dichloromethane, chloroform, carbon tetrachloride or a mixture of two or more of the aforementioned chlorinated aliphatic solvents) or a chlorinated aromatic solvent (such as, in particular, chlorobenzene, dichlorobenzene or a mixture of the two). The reaction can be performed as a solution polymerization or suspension polymerization.

The isolation of the polyamine formed in the reaction of step (A) can be effected by known methods that are customary in the specialist field; particular mention should be made of filtration, distillation, sublimation, crystallization, precipitation or a combination of two or more of these methods. Which of these is the most suitable in the individual case will be apparent to the person skilled in the art from the reaction conditions employed, and can if required be ascertained by simple preliminary experiments.

Reaction of the Polyamine with Phosgene (Step (B))

In the next step, the polyamine obtained in step (A) is phosgenated. This is preferably accomplished at a temperature in the range from 0° C. to 200° C., more preferably 5° C. to 180° C., most preferably 5° C. to 150° C.

The reaction with phosgene is preferably effected using a stoichiometric excess of phosgene, based on the amino groups of the polyamine. The solvent used for the phosgenation is preferably toluene, xylene, chlorobenzene, dichlorobenzene (especially the ortho isomer), dioxane, methylene chloride, perchloroethylene, trichlorofluoromethane or a mixture of two or more of the aforementioned solvents.

Further Reaction of the Polyisocyanate (Step (C))

All reactions of the isocyanates that are known in the specialist field are possible options for the further use of the polyisocyanate prepared in accordance with the invention. For instance, the polyisocyanate obtained in step (B) can be reacted in a step (C)(i) with an organic compound comprising 2 or more acidic hydrogen atoms to obtain a polyaddition product (so-called 2-component polyurethane products). Acidic hydrogen atoms in the context of the present invention refer to hydrogen atoms bonded to N, O or S, when they afford methane by reaction with methylmagnesium iodide. This method was developed by Zerewitinoff, and for that reason acidic hydrogen atoms are also referred to as Zerewitinoff-active hydrogen atoms in this sense.

Examples of useful compounds having 2 or more acidic hydrogen atoms include polyols (third polyol). In this way, it is possible to obtain polyurethane elastomers, polyurethane thermoplastics, polyurethane foams, polyurethane adhesives (see also DE 10 2009 008 867) and polyurethane sealants.

Useful compounds having 2 or more acidic hydrogen atoms additionally also include polyamines (including the amines obtained in step (A) of the process of the invention).

In this way, it is possible to obtain polyurea elastomers, polyurea thermoplastics, polyurea foams, polyurea adhesives and polyurea sealants.

It is of course likewise possible to use mixtures of polyols and polyamines as compounds having 2 or more acidic hydrogen atoms, which gives rise to polyaddition products having mixed urethane and urea structures.

It is likewise possible to react the polyisocyanates obtained in step (B) with (a substoichiometric amount of) water (in relation to the isocyanate groups present) (step (C)(ii), which follows after step (B)). In this way, it is possible to obtain foams, adhesives or sealants, especially as what are called 1-component products (DE 10 2009 005 017). In 1-component systems, the water comes from a gas atmosphere surrounding the polyisocyanate (generally air), or from a substrate (a water-containing surface) on which the polyisocyanate is present (or to which it has been applied).

One- or two-component formulations according to step (C), owing to the complete absence of monomeric isocyanates, may especially also be used in the medical sector (see WO 2009/100853 for use examples). In this field of application, it is advantageous in the case of 2-component systems to use the polyamines from step (A) as compound having 2 or more acidic hydrogen atoms or water.

In relation to the polyisocyanate of the invention, the statements made above with regard to the process of the invention are correspondingly applicable, and so there is no need for repetition. When using fermentatively produced anthranilic acid, the polyisocyanate has a proportion by mass of biogenic carbon based on its total mass in the range from 0.60% to 46%, preferably from 1.5% to 43%, more preferably from 7.0% to 41%. The crucial test method here is ASTM D 6866-21 (DOI: 10.1520/D6866-21).

As likewise described in connection with the description of the process of the invention, the polyisocyanates of the invention may be used for preparation of a polyaddition product by reaction with a compound comprising 2 or more acidic hydrogen atoms, in which case the statements made above in connection with the process are again correspondingly applicable. In particular, in the context of the use of the invention, the compound comprising 2 or more acidic hydrogen atoms may comprise a third polyol and/or water. The same is of course applicable to the polyaddition products of the invention that are formed from the polyisocyanate of the invention and a compound comprising 2 or more acidic hydrogen atoms.

The invention is more particularly elucidated hereinafter with reference to examples.

EXAMPLES

Preparation of the polyamines (step (A))
Methods of Analysis:

Dynamic viscosity: determined by Anton Paar MCR 51 rheometer to DIN 53019 (09-2008).

NCO content: determined to DIN 53185 (05-1997).

OH number (hydroxyl number): determined in accordance with DIN 53240-2 (2007-11), except, in a departure from that standard, using pyridine rather than THF/dichloromethane as solvent. Titration was effected with 0.5 molar ethanolic KOH (endpoint recognition by potentiometry). The reporting of the unit in "mg/g" relates to mg[KOH]/g [polyol].

Amine value: determined to DIN EN ISO 2114 (June 2002).

Acid number: determined to DIN EN ISO 2114 (June 2002).

Melting point (m.p.): determined according to Europaisches Arzneibuch[European Pharmacopoeia] 10.0, Deutscher Apotheker Verlag, 2020, ISBN 978-3-7692-7515-5, pages 41 to 42

Feedstocks:

Polyol 1:
Polyetherpolyol prepared from trimethylolpropane as starter and ethylene oxide under KOH catalysis. OH number 550 mg/g, OH functionality=3.

Polyol 2:
Polyetherpolyol prepared from 1,2-propylene glycol as starter and ethylene oxide under KOH catalysis. OH number 195 mg/g, OH functionality=2.

Polyol 3:
Ethylene glycol, CAS RN 107-21-1, Fa. INEOS Phenol GmbH+Co.KG (DE), ≥99.5%.

Polyol 4:
Diethylene glycol, CAS RN 111-46-6, Fa. INEOS Phenol GmbH+Co.KG (DE), ≥99%.

Isatoic Anhydride:
Isatoic anhydride, CAS RN 118-48-9, Sigma-Aldrich Chemie GmbH, about 98%.

Acetone:
Acetone, CAS RN 67-64-1, Sigma-Aldrich Chemie GmbH, about 99.8%.

NaOH:
Solid sodium hydroxide, CAS RN 1310-73-2, Sigma-Aldrich Chemie GmbH, about 98%.

KOH:
Potassium hydroxide, CAS RN 1310-58-3, Sigma-Aldrich Chemie GmbH, 90-92%

Dioxane:
1,4-Dioxane, CAS RN 123-91-1, Sigma-Aldrich Chemie GmbH, ≥99.9%

Isopropanol:
Isopropyl alcohol, CAS RN 67-63-0, Kraemer & Martin GmbH, ≥99.5%

Methanol:
Methanol, CAS RN 67-56-1, Sigma-Aldrich Chemie GmbH, ≥99.5%

Polyamine A:
A 1 L multineck flask fitted with stirrer, heating mantle and reflux condenser was initially charged with 153 g of polyol 1, 294 g of polyol 2 (which overall constitute the first polyol), 379 g of isatoic anhydride, 15 g of NaOH and 500 g of acetone at room temperature, which were heated gradually to 85° C. over 2 hours, in the course of which $CO_2$ escaped in gaseous form. On conclusion of evolution of gas, the reflux condenser was replaced by a distillation system. Acetone was distilled at 85° C., first at ambient pressure and then at a reduced pressure of 300 $mbar_{(abs.)}$. Finally, the acetone was removed at 15 $mbar_{(abs.)}$ and 85° C. The remaining bottoms were filtered through a 125 μm sieve. This gave 730 g of a brownish viscous liquid. The amount of $CO_2$ that had escaped corresponded, within the scope of measurement accuracy, to the value to be theoretically expected in the case of full conversion. The polyamine A obtained was liquid at room temperature and had the following properties:

Amine value: 178.1 mg/g; acid number: 0.7; OH number: 24.2 mg/g; viscosity: 35,000 mPa·s at 25° C.

Polyamine B:
A 1 L multineck flask fitted with stirrer, heating mantle and reflux condenser was initially charged with 153 g of polyol 1, 294 g of polyol 2 (which overall constitute the first polyol), 407 g of isatoic anhydride, 15 g of NaOH and 500 g of acetone at room temperature. The further procedure corresponded to that of the preparation of polyamine A. 744 g of a brownish viscous liquid was obtained. Again, the amount of $CO_2$ that had escaped corresponded, within the scope of measurement accuracy, to the value to be theoretically expected in the case of full conversion. The polyamine B obtained was liquid at room temperature and had the following properties:

Amine value: 187.7 mg/g; acid number: 0.3; OH number: 4.7 mg/g; viscosity: 69, 700 mPa·s at 25° C.

Polyamine C:

A 2 L multineck flask fitted with stirrer, heating mantle and reflux condenser was initially charged with 31 g of polyol 3, 163 g of isatoic anhydride, 2.8 g of KOH and 280 g of dioxane at room temperature. The reaction solution was heated to 80° C. within about 2 h, in the course of which $CO_2$ escaped in gaseous form. Subsequently, 280 g of isopropanol was added. The product was then precipitated by adding 560 mL of distilled water, filtered off and washed with isopropanol. The solid was dried at 80° C. in a drying cabinet overnight. 132 g (88% of theory) of a brownish solid was obtained. Again, the amount of $CO_2$ that had escaped corresponded, within the scope of measurement accuracy, to the value to be theoretically expected in the case of full conversion. The polyamine C obtained was solid at room temperature and had the following properties:

Amine value: 376.4 mg/g; acid number: 0.6; m.p. 128° C.

Pol amine D:

A 2 L multineck flask fitted with stirrer, heating mantle and reflux condenser was initially charged with 55.3 g of polyol 4, 163 g of isatoic anhydride, 2.8 g of KOH and 280 g of dioxane at room temperature. The reaction solution was heated to 75° C. within about 1 h, in the course of which $CO_2$ escaped in gaseous form. Subsequently, 280 g of methanol was added. The product was then precipitated by adding 560 mL of distilled water, filtered off and washed with methanol. The solid was dried at 80° C. in a drying cabinet overnight. 154 g (89.5% of theory) of a brownish solid was obtained. Again, the amount of $CO_2$ that had escaped corresponded, within the scope of measurement accuracy, to the value to be theoretically expected in the case of full conversion. The polyamine D obtained was solid at room temperature and had the following properties:

Amine value: 329.2 mg/g; acid number: 0.3; m.p. 105° C.

Preparation of the Polvisocvanates (Step (B))

Methods of Analysis:

The NCO value was determined by reacting a sample of the isocyanate with excess di-n-butylamine, followed by back titration of the excess amine with a hydrochloric acid standard solution.

Dynamic viscosity was measured at 25° C. using a falling ball viscometer.

Total chlorine content was determined by x-ray fluorescence analysis.

Example 1 (Polyisocyanate A)

The apparatus used consisted of a 2 L multineck flask fitted with stirrer, dropping funnel, reflux condenser, gas inlet tube and distillation attachment, where dropping funnel, reflux condenser, gas inlet tube and distillation attachment were each provided with a stop valve. An initially charged solution of 220 g of phosgene in 640 mL of dry chlorobenzene was stirred in said multineck flask at 0° C. The distillation attachment was at first isolated from the apparatus by the stop valve. A dropping funnel was used to add a solution of 120 g of polyamine A in 560 mL of dry chlorobenzene that had been heated to 70° C. all at once while stirring. The resulting suspension was heated gradually to 100° C. over the course of 1 h while stirring. This was followed by heating to reflux temperature within 10 min while stirring. The reaction mixture was kept under reflux for about a further 15 min. During the heating and reflux phases, gaseous phosgene was introduced continuously into the reaction mixture at a flow rate of 10 standard liters/h.

Subsequently, the phosgene stream was broken, the reflux condenser was shut off using a valve, and the valve to the distillation attachment was opened, in order to very substantially distill off the solvent in a water-jet vacuum (about 20 $mbar_{(abs.)}$).

The remaining distillation bottoms were transferred to a distillation apparatus. At a pressure at the top of the distillation apparatus of about 1-2 $mbar_{(abs.)}$ and at a temperature of the heating medium for the distillation still in the range from 220 to 230° C., the rest of the chlorobenzene was distilled off over the course of about 22 min. Thereafter, the bottom product was rapidly cooled down to room temperature and characterized:

The NCO value was 11.5%, the viscosity 2175 mPa·s, and the total chlorine content 1.67%. The product that had been cooled down to room temperature was liquid.

Example 2 (Polvisocvanate B)

Analogously to example 1 (i.e. with the same phosgene excess), the phosgenation of 124 g of polyamine B was conducted. The resulting bottom product had an NCO value of 11.4%, a viscosity of 3241 mPa·s and a total chlorine content of 1.29%. The product that had been cooled down to room temperature was liquid.

Example 3 (Polvisocvanate C— Comparison)

The apparatus used consisted of a 500 mL multineck flask fitted with stirrer, dropping funnel, reflux condenser, gas inlet tube and distillation attachment, where dropping funnel, reflux condenser, gas inlet tube and distillation attachment were each provided with a stop valve. An initially charged solution of 32 g of phosgene in 80 mL of dry chlorobenzene was stirred in said multineck flask at −10° C. The solution of 22.5 g of polyamine C in 150 mL of dry chlorobenzene that had been heated to 70° C. was added all at once while stirring. The resulting suspension was heated gradually to 95° C. over the course of 40 min while stirring. This dissolved the solids. This was followed by heating to reflux temperature within 10 min while stirring. The reaction mixture was kept under reflux for about a further 10 min. During the heating and reflux phases, gaseous phosgene was introduced continuously into the reaction mixture at a flow rate of 5 standard liters/h.

Subsequently, the phosgene stream was broken, the reflux condenser was shut off using a valve, and the valve to the distillation attachment was opened, in order to very substantially distill off the solvent in a water-jet vacuum (about 20 $mbar_{(abs.)}$).

The remaining distillation bottoms were transferred to a distillation apparatus. At a pressure at the top of the distillation apparatus of about 1-2 $mbar_{(abs.)}$ and at a temperature of the heating medium for the distillation still of 150° C., the rest of the chlorobenzene was distilled off over the course of about 20 min. Thereafter, the bottom product was rapidly cooled down to room temperature and characterized. The resulting bottom product had an NCO value of 24.05% and was solid at room temperature. The melting point was ascertained as 109.3° C.

Example 4 (Polyisocyanate D— Comparison)

The apparatus used consisted of a 2 L multineck flask fitted with stirrer, dropping funnel, reflux condenser, gas inlet tube and distillation attachment, where dropping funnel, reflux condenser, gas inlet tube and distillation attachment were each provided with a stop valve. An initially charged solution of 32 g of phosgene in 80 mL of dry chlorobenzene was stirred in said multineck flask at –5° C. The solution of 21.9 g of polyamine D in 105 mL of dry chlorobenzene that had been heated to 70° C. was added all at once while stirring, forming an oily mixture. The resulting mixture was heated gradually to 80° C. over the course of 25 min while stirring, until a solution had formed. This was followed by heating to reflux temperature within about 30 min while stirring. The reaction mixture was kept under reflux for about a further 20 min. During the heating and reflux phases, gaseous phosgene was introduced continuously into the reaction mixture at a flow rate of 5 standard liters/h.

Subsequently, the phosgene stream was broken, the reflux condenser was shut off using a valve, and the valve to the distillation attachment was opened, in order to very substantially distill off the solvent in a water-jet vacuum (about 20 mbar$_{(abs.)}$).

The remaining distillation bottoms were transferred to a distillation apparatus. At a pressure at the top of the distillation apparatus of about 1-2 mbar$_{(abs.)}$ and at a temperature of the heating medium for the distillation still of 150° C., the rest of the chlorobenzene was distilled off over the course of about 20 min. Thereafter, the bottom product was rapidly cooled down to room temperature and characterized. The resulting bottom product had an NCO value of 21.35% and was solid at room temperature. The melting point was ascertained as 90.7° C.

The invention claimed is:

1. A process for preparing a polyisocyanate comprising:
(A) reacting an anthranilic acid derivative comprising anthranoyl halide, isatoic anhydride or a mixture thereof with a first polyol of functionality b and the general formula X—(OH)$_b$, where b has a value of 2 to 8 and X is a radical that derives from the first polyol by removal of all alcohol groups, and where the first polyol has a number-average molar mass of at least 200 g/mol, to obtain a polyamine of the formula $$H_2N-(\text{ortho-}C_6H_4)-(CO)-O-X-[-O-(CO)-(\text{ortho-}C_6H_4)-NH_2]_a$$

in which a=b–1; and
(B) reacting the polyamine with phosgene to obtain a polyisocyanate of the formula $$OCN-(\text{ortho-}C_6H_4)-(CO)-O-X-[-O-(CO)-(\text{ortho-}C_6H_4)-NCO]_a.$$

2. The process as claimed in claim 1, in which the first polyol comprises a polyether polyol, a polyester polyol, a polyetherester polyol, a polycarbonate polyol, a polyether polycarbonate polyol, a polythioether polyol or a mixture of two or more thereof.

3. The process as claimed in claim 1, in which the reaction of the anthranilic acid derivative with the first polyol is conducted in the presence of a basic catalyst.

4. The process as claimed in claim 1, in which the reacting of the anthranilic acid derivative with the first polyol is conducted at a temperature of 0° C. to 120° C.

5. The process as claimed in claim 1, in which a gas formed in step (A) is removed in gaseous form, chemically bound or physically bound during the reaction of the anthranilic acid derivative with the first polyol.

6. The process as claimed in claim 1, in which the polyamine obtained in step (A) is isolated by a method comprising filtration, distillation, sublimation, crystallization, precipitation or a combination of two or more thereof.

7. The process as claimed in claim 1, in which the reacting of the polyamine with phosgene in step (B) is conducted at a temperature of 0° C. to 200° C.

8. The process as claimed in claim 1, in which phosgene is used in step (B) in a stoichiometric excess based on the amino groups of the polyamine.

9. The process as claimed in claim 1, in which step (B) is followed by:
(C)(i) reacting the polyisocyanate obtained in step (B) with an organic compound comprising 2 or more acidic hydrogen atoms to obtain a polyaddition product.

10. The process as claimed in claim 9, in which the organic compound comprising 2 or more acidic hydrogen atoms comprises a third polyol and/or a polyamine, and the polyaddition product obtained is an elastomer, a thermoplastic, a foam, an adhesive or a sealant.

11. The process as claimed in claim 1, in which step (B) is followed by:
(C)(ii) reacting the polyisocyanate obtained in step (B) with water to obtain a foam, an adhesive, or a sealant.

12. A polyisocyanate of the formula $$OCN-(\text{ortho-}C_6H_4)-(CO)-O-X-[-O-(CO)-(\text{ortho-}C_6H_4)-NCO]_a$$

in which
X is a radical which derives from a first polyol having a number-average molar mass of at least 200 g/mol, having functionality b, and being of the general formula X—(OH)$_b$, where b has a value of 2 to 8, by removal of all alcohol groups, and in which a=b–1.

13. A method of producing a polyaddition product, comprising reacting the polyisocyanate as claimed in claim 12 with a compound comprising 2 or more acidic hydrogen atoms.

14. The method as claimed in claim 13, in which the compound comprising 2 or more acidic hydrogen atoms comprises a third polyol, a polyamine and/or water.

15. A polyaddition product formed from a polyisocyanate as claimed in claim 12 and a compound comprising 2 or more acidic hydrogen atoms.

* * * * *